(12) United States Patent
Noetzel et al.

(10) Patent No.: US 7,479,393 B2
(45) Date of Patent: Jan. 20, 2009

(54) ANALYTICAL TEST ELEMENT AND METHOD FOR BLOOD ANALYSES

(75) Inventors: Siegfried Noetzel, Wilhelmsfeld (DE); Jean-Philippe Bogardi, Mannheim (DE); Dieter Mangold, Maxdorf (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 804 days.

(21) Appl. No.: 10/774,247

(22) Filed: Feb. 6, 2004

(65) Prior Publication Data

US 2004/0191124 A1 Sep. 30, 2004

(30) Foreign Application Priority Data

Feb. 7, 2003 (DE) ................... 103 05 050

(51) Int. Cl.
*G01N 1/18* (2006.01)
*G01N 1/10* (2006.01)
*G01N 33/48* (2006.01)
*G01N 33/72* (2006.01)

(52) U.S. Cl. ................ 436/179; 436/63; 436/66; 436/67; 436/174; 436/175; 436/177; 436/178; 436/180; 422/99; 422/100; 422/101; 422/102; 435/2

(58) Field of Classification Search .......... 436/63, 436/66, 67, 174, 175, 177, 178, 179, 180; 422/68.1, 59, 99, 100, 101, 102, 103, 9; 435/2
See application file for complete search history.

(56) References Cited

U.S. PATENT DOCUMENTS

| 4,675,117 A | * | 6/1987 | Neumann et al. ........... 210/789 |
| 6,143,510 A | * | 11/2000 | Hoshino et al. ............ 435/7.94 |
| 6,319,719 B1 | * | 11/2001 | Bhullar et al. ................ 436/70 |
| 6,406,672 B1 | * | 6/2002 | Bhullar et al. .............. 422/101 |
| 6,475,441 B1 | | 11/2002 | Parce et al. |
| 6,521,182 B1 | * | 2/2003 | Shartle et al. ................ 422/58 |
| 7,087,203 B2 | * | 8/2006 | Gordon et al. ................ 422/72 |
| 2003/0003522 A1 | | 1/2003 | Goldman ................... 150/162 |

FOREIGN PATENT DOCUMENTS

| DE | 43 23 672 A | 1/1995 |
| EP | A 0989407 | 9/1999 |
| WO | WO 99/18436 A | 4/1999 |
| WO | WO0062931 A1 | 10/2000 |
| WO | WO 01/24931 A | 4/2001 |

* cited by examiner

*Primary Examiner*—Maureen M Wallenhorst

(57) ABSTRACT

An analytical test element for blood analyses is provided having at least a substrate body having a channel structure for the flow transport of a blood sample from an application site to at least one analytical site. The channel structure has a dilution channel that can be loaded with the blood sample and is provided with a separation component for retaining corpuscular blood components and has a sample channel which conveys a blood sample aliquot to be diluted and joins the dilution channel at a mixing site.

19 Claims, 1 Drawing Sheet

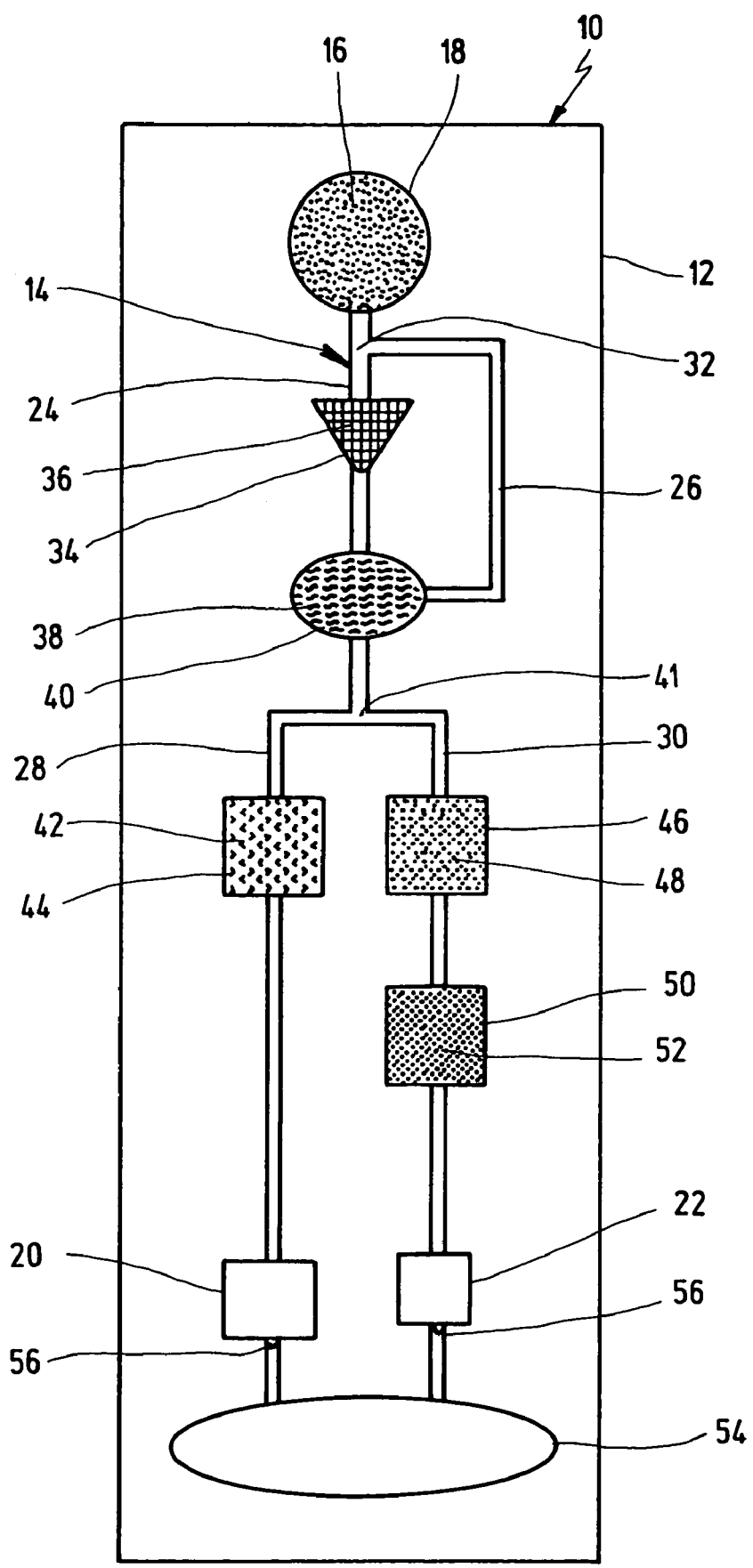

ANALYTICAL TEST ELEMENT AND METHOD FOR BLOOD ANALYSES

PRIORITY CLAIM

The application claims priority under 35 U.S.C. §119 to German Application No. 103 05 050.7 filed Feb. 7, 2003.

DESCRIPTION

The invention concerns an analytical test element for blood analyses especially by means of a single-use rapid test comprising a substrate body having a preferably microfluidic channel structure for the flow transport of a blood sample from an application site to at least one analytical site. The invention also concerns a corresponding method for carrying out blood analyses in which a blood sample is conveyed by means of a channel structure in an analytical test element from an application site to at least one analytical site.

A test element of this type is known from WO 01/24931. This application describes a channel or flow structure that is specially designed for separating plasma or serum from a whole blood sample and comprises two capillary-active zones where a first zone is composed of a porous matrix material and a second zone which is in contact with the first zone comprises one or more capillary channels. As a result the plasma obtained in the first zone is made available in the second zone free from interfering components as a target fluid for example for glucose tests.

A test element is generally understood as a carrier-bound fluidic (micro)system for receiving a liquid sample which enables sample preparation for an immediate or later analysis independent of a laboratory environment. Such test elements are usually intended to be single-use articles or disposables for near patient diagnostics in which all reagents that are necessary to carry out the test are provided on the carrier or component so that they can also be used by laymen without requiring special handling.

Such test elements are used as test strips especially for blood glucose monitoring by diabetics. On the other hand, the determination of haemoglobin A1c allows a retrospective estimate of the average glucose concentration over the last weeks and thus of the quality of the metabolic control of the diabetic. HbA1c is defined as haemoglobin A that has been glycated with glucose on the N-terminal valine residues of the β chains. HbA1c is usually stated as a percentage of the total haemoglobin which requires a determination of the haemoglobin concentration from the same blood sample in addition to the HbA1c content. This double determination of Hb and HbA1c has previously been carried out on laboratory instruments that are very complicated to operate and are thus error-prone and expensive.

Hence the object of the invention is to avoid the disadvantages occurring in the prior art and to improve a test element such that blood tests can be carried out cheaply with as little interaction by the user as possible and low consumption of reagents especially when the analyte is present at a high concentration in the initial sample.

The combination of features stated in the independent patent claims is proposed to achieve this object. Advantageous embodiments and further developments of the invention are derived from the dependent claims.

Accordingly the invention proposes that the channel structure has a dilution channel that can be loaded with a blood sample and contains separation means for retaining corpuscular blood components, and a sample channel for conveying an aliquot of a blood sample to be diluted which is joined to the dilution channel at a mixing site. This enables whole blood that has been applied by the user to be diluted with its own liquid components without having to store additional liquids. The dilution with the sample material is automatically controlled by the flow transport which obviates complicated manual handling steps by the user or complex mechanical interactions by an analyzer.

The blood sample can be advantageously applied to the sample channel and the dilution channel via a junction which also divides the sample flow. In this connection the blood sample can be applied to a central point and be divided at the junction or at a branch of the sample channel in a quantified, predefined ratio such that the sample channel and dilution channel can be loaded with the sample. In order to set a specified ratio for dividing the partial currents of the blood sample that are passed through, it is advantageous when the relative channel cross-sections of the sample and dilution channel are appropriately adapted. In order to reduce the haemoglobin concentration, it is especially advantageous when the rate of flow through the dilution channel is more than 10-times and preferably more than 100-times the rate of flow through the sample channel.

In order to retain cell components it is advantageous when a filter element especially comprising a glass fibre fleece or a microporous filter matrix or filter membrane is located as a separation means in the dilution channel and preferably in a filter chamber. Alternatively or in addition, the dilution channel can have a microstructure geometry designed to retain cell components of the blood sample as the separation means.

Another advantageous embodiment provides that the mixing site comprises a lysis chamber provided with a lysing agent to haemolyse the diluted blood sample.

One aspect and another variant of the invention provides that the channel structure has a first analytical channel for determining the total haemoglobin value (Hb) of the blood sample and a second analytical channel for determining a glycohaemoglobin value (HbA1c) of the blood sample. This enables a HbA1c test to be carried out in allocated flow paths in a one-step test by a simple application of blood to a test element.

An advantageous embodiment provides that the analytical channels are arranged in parallel and can be loaded with the diluted blood sample by means of a branch acting as a current divider downstream of the mixing site.

It is advantageous for the determination of total haemoglobin when the first analytical channel has an oxidation chamber containing an incorporated oxidizing agent and especially ferricyanide to oxidize the released haemoglobin.

The second analytical channel is advantageously designed for the immunoturbidi-metric determination of the glycohaemoglobin concentration. For this purpose the second analytical channel advantageously has a first reaction chamber into which HbA1c antibodies are dispensed and this first reaction chamber is followed by a second reaction chamber containing an agglutinator.

Other basic methods for determining HbA1c in blood are also known to a person skilled in the art for example from EP-A-0 989 407. These methods can also be used in the present invention and are therefore explicitly incorporated.

The end sections of the analytical channels are designed as cuvettes for photometric analysis and thus form analytical sites for a simple, contactless detection.

In order to collect the sample liquid safely and hygienically, it is advantageous when the analytical channels discharge into a collecting reservoir.

An automatic flow transport is achieved by the channel structure having a wholly or partially capillary geometry. It is advantageous for the control of flow transport when the channel structure has wall sections that have for example been modified by surface treatment, plasma treatment or coating. Another advantageous embodiment provides that the channel structure has valve elements to control the flow transport that are in particular in the form of hydrophilic or hydrophobic channel sections. However, it is basically also possible for the flow transport in the channel structure to be controlled externally by external control means acting on the substrate body and in particular by local application of pressure or centrifugal forces.

With regard to the methodology the object mentioned above is achieved by obtaining liquid components from the blood sample that are introduced into a portion of the blood sample to be analysed for the purposes of dilution. An advantageous embodiment provides that a whole blood sample as the starting material is fed into a dilution channel and a sample channel of the channel structure in parallel subflows and that the subflow in the dilution channel which has been depleted of cell components is joined with the subflow in the sample channel at a mixing site.

BRIEF DESCRIPTION OF THE DRAWING

The invention is elucidated in more detail in the following on the basis of an example of application shown schematically in the drawing. The single FIGURE shows an analytical test element for determining Hb and HbA1c values of a blood sample in a rapid test.

The test element 10 comprises an elongate support or substrate body 12 containing a channel structure 14 formed therein for the flow transport of microscopic sample quantities (μl) of a blood sample 16 to be analysed from an application zone 18 to measuring or analytical sites 20, 22 for Hb and HbA1c.

The substrate body 12 can be formed from plastic as an injection-moulded part or from several layers of foil as a composite part. It is designed to be a consumable or a so-called disposable for a single-use test.

The channel structure 14 can be directly moulded into the substrate body or be formed by special manufacturing steps such as embossing or stamping. At least sections thereof have a suitable capillary geometry for an automatic capillary-active flow transport of the blood fluid.

Starting from the application zone 18 the channel structure 14 has a dilution channel 24, an aliquot or sample channel 26 and two analytical channels 28, 30 leading to the analytical sites 20, 22.

The blood sample 16 can be fed via a junction 32 into the dilution channel 24 and the sample channel 26 whereby the sample flow is split in parallel. Due an appropriate design of the channel cross-sections, the flow rate through the dilution channel 24 is many times higher than the flow rate through the sample channel 26.

The dilution channel 24 contains a separation means 36 in a separation chamber 34 for retaining cell components of the portion of the blood sample 16 that flows through it. Such separation means 36 can for example be in the form of a glass fibre fleece located in the separation chamber 34.

The dilution channel 24 and the sample channel 26 discharge into a mixing or lysing chamber 40 containing a lysing agent 38. The outlet side communicates via a branch 41 as a flow divider with the analytical channels 28, 30.

An oxidation chamber 44 containing an oxidizing reagent 42 such as potassium hexacyanoferrate is located in the first analytical channel 28 for oxidizing released haemoglobin. The analytical site 20 located downstream thereof is designed as a cuvette for a photometric determination of Hb.

The second analytical channel 30 is used for the immunoturbidimetric determination of glycated haemoglobins. For this purpose it has a first reaction chamber 46 containing HbA1c antibodies 48 dispensed therein and a subsequent second reaction chamber 50 containing an agglutination agent 52 for excess HbA1c antibodies. The second analytical site 22 is located downstream thereof and is also designed as a cuvette for a photometric measurement of turbidity.

Both analytical channels 20, 22 discharge into a common collecting reservoir 54 as waste for the examined liquid samples. Barriers or valve elements 56 comprising hydrophilic or hydrophobic surface modifications may be located on the outlet side of the cuvettes 20, 22 and optionally of the chambers 40, 44, 46, 50 to control the flow transport. These elements allow a control of reaction processes and in particular the control of the sample volume and measuring process, the dissolution of incorporated dry reagents and their mixing in the reaction chambers e.g. by temporarily interrupting the liquid flow.

In order to carry out an in vitro rapid test for determining glycated haemoglobin, a small amount of whole blood is applied by a user to the application zone 18. An aliquot thereof is conveyed via the sample channel 26 into the lysing chamber 40 and is mixed there with the plasma obtained by removing erythrocytes in the dilution channel 24. This results in a defined dilution or reduction of the analyte concentration without having to process additional dilution liquids. At the same time the sample is mixed in the lysing chamber 38 with the lysing agent 38 (for example saponin) provided as a dry substance which lyses the erythrocytes and releases the red-pigmented haemoglobin.

A portion of the diluted haemolysate is conveyed via the branch 41 into the first analytical channel 28 and is converted in the oxidation chamber 44 into a derivative having a characteristic spectrum. After it has passed into the cuvette 20, the total haemoglobin concentration Hb can be measured by a photometer that is not shown.

For the glycohaemoglobin determination another portion of the diluted haemolysate is passed via the branch 41 into the second analytical channel 30. In the first reaction chamber of this channel the glycohaemoglobin HbA1c from the sample is mixed with an excess of HbA1c antibodies 48 and converted into a soluble antigen-antibody complex. The remaining free antibodies 48 are agglutinated in the second reaction chamber 50 and subsequently measured turbidimetrically in the cuvette 22. The change in turbidity is inversely proportional to the amount of bound glyco-haemoglobin. The final result is subsequently calculated as a ratio of HbA1c to Hb.

The test procedure described above enables a one-step procedure without having to store or add additional liquids. It is obvious that the controlled dissolution of dispensed and dried reagents in automatically regulated microfluidic reaction paths also enables other embodiments of a HbA1c test which also include the use of other methods of determination in which the plasma volume obtained can also be used in subsequent process steps e.g. to wash out excess reagents. It is basically possible for the Hb and HbA1c determination to be carried out in channel sections arranged in series and optionally also without prior sample dilution. It is also conceivable that at least a part of the channel structure is formed by a porous matrix material.

The invention claimed is:

1. An analytical test element comprising: an application site, a microfluidic channel structure in fluid communication with said application site, and at least one analytical site in fluid communication with said microfluidic channel structure, wherein the channel structure comprises a dilution channel for receiving a first portion of a blood sample applied to the application site which comprises separation means for retaining corpuscular blood components of said first portion, and a sample channel for receiving a second portion of the blood sample applied to the application site which conveys the second portion to a mixing site located at a point where the sample channel joins the dilution channel downstream of the separation means in order to dilute the second portion of the blood sample.

2. The analytical test element of claim 1, further comprising a junction in the channel structure downstream of said application site, configured such that a blood sample applied to the application site will flow into both the sample channel and the dilution channel in parallel.

3. The analytical test element of claim 1, wherein the channel cross-sections of the sample and dilution channel are adjusted relative to one another to set a predetermined dividing ratio for the blood sample that passes through.

4. The analytical test element of claim 1, wherein the sample flows through the dilution channel at a rate that is more than 10-fold higher than the rate the sample flows through the sample channel.

5. The analytical test element of claim 1, wherein the sample flows through the dilution channel at a rate that is more than 100-fold higher than the rate the sample flows through the sample channel.

6. The analytical test element of claim 1, wherein a filter element is disposed as a separation means in the dilution channel.

7. The analytical test element of claim 6, wherein the filter element comprises a glass fibre fleece or a microporous filter matrix or filter membrane.

8. The analytical test element of claim 1, wherein the dilution channel has a microstructure geometry designed to retain cell components of the blood sample as a separation means.

9. The analytical test element of claim 1, wherein the mixing site further comprises a lysing chamber provided with a lysing agent to haemolyse the blood sample.

10. The analytical test element of claim 1, wherein the channel structure comprises a first analytical channel to determine the total haemoglobin value (Hb) of the blood sample and a second analytical channel for determining a glycohaemoglobin value (HbA1c) of the blood sample, wherein said first and said second analytical channels are positioned downstream of said mixing site.

11. The analytical test element of claim 10, wherein the analytical channels can be loaded with the blood sample via a branch acting as a flow divider downstream of the mixing site.

12. The analytical test element of claim 1, wherein the channel structure at least in a section thereof has a capillary geometry for an automatic capillary-active flow transport.

13. The analytical test element of claim 12, wherein the channel structure has wall structures for regulating the flow transport.

14. The analytical test element of claim 13, wherein the wall structures are modified by surface treatment, plasma treatment or coating.

15. The analytical test element of claim 12, wherein the channel structure has valve elements for regulating the flow transport.

16. The analytical test element of claim 15, wherein the valve elements are formed by hydrophilic or hydrophobic channel sections.

17. The analytical test element of claim 12, wherein the flow transport in the channel structure is regulated by local application of pressure or centrifugal forces.

18. A method for carrying out blood analyses comprising providing an analytical test element comprising an application site, a microfluidic channel structure in fluid communication with said application site, and at least one analytical site in fluid communication with said microfluidic channel structure, applying a blood sample to be analyzed to said application site, moving said blood sample via said microfluidic channel structure from said application site to said at least one analytical site, obtaining liquid components from a first portion of the blood sample applied to the application site by passing the first portion through a dilution channel of the channel structure comprising separation means for retaining corpuscular blood components, and adding said liquid components to a second portion of the blood sample applied to the application site and conveyed through a sample channel of the channel structure, wherein the liquid components are added to the second portion of the blood sample at a mixing site located at a point where the sample channel joins the dilution channel downstream of the separation means.

19. The method of claim 18 further comprising applying a whole blood sample to the application site, feeding said whole blood sample in parallel subflows into said dilution channel and said sample channel of the channel structure, depleting at least a portion of said whole blood sample of its cell components in the dilution channel, and joining the dilution channel subflow and the sample channel subflow at said mixing site positioned downstream of said dilution channel subflow and said sample channel subflow.

* * * * *